US010626437B2

(12) United States Patent
Deol et al.

(10) Patent No.: US 10,626,437 B2
(45) Date of Patent: Apr. 21, 2020

(54) METHODS FOR INACTIVATION AND EXTRACTION OF ACID-FAST BACTERIA FROM LIQUID MEDIA FOR CHARACTERIZATION AND/OR IDENTIFICATION USING MASS SPECTROMETRY

(71) Applicant: bioMérieux, Inc., Durham, NC (US)

(72) Inventors: Parampal Deol, Raleigh, NC (US); Eric Miller, Raleigh, NC (US); Erik Moreno, Raleigh, NC (US); Heather Totty, Hillsborough, NC (US)

(73) Assignee: bioMerieux, Inc., Durham, NC (US)

( * ) Notice: Subject to any disclaimer, the term of this patent is extended or adjusted under 35 U.S.C. 154(b) by 14 days.

(21) Appl. No.: 15/211,245

(22) Filed: Jul. 15, 2016

(65) Prior Publication Data

US 2017/0058316 A1 Mar. 2, 2017

Related U.S. Application Data

(60) Provisional application No. 62/306,390, filed on Mar. 10, 2016, provisional application No. 62/209,116, filed on Aug. 24, 2015.

(51) Int. Cl.
| | | |
|---|---|---|
| C12Q 1/24 | (2006.01) | |
| G01N 33/68 | (2006.01) | |
| C12N 1/02 | (2006.01) | |
| C12M 1/00 | (2006.01) | |
| B01L 3/00 | (2006.01) | |

(52) U.S. Cl.
CPC ............... *C12Q 1/24* (2013.01); *C12M 47/02* (2013.01); *C12N 1/02* (2013.01); *G01N 33/6851* (2013.01); *B01L 3/5021* (2013.01); *G01N 2333/195* (2013.01); *G01N 2333/35* (2013.01); *G01N 2333/355* (2013.01)

(58) Field of Classification Search
CPC .................. C12Q 1/24; G01N 33/6851; G01N 2333/355; G01N 2333/35; G01N 2333/195; C12M 47/02; C12N 1/02; B01L 3/5021
See application file for complete search history.

(56) References Cited

U.S. PATENT DOCUMENTS

| | | | | |
|---|---|---|---|---|
| 5,253,551 A * | 10/1993 | DeVaughn | ............ | B01L 3/5021 |
| | | | | 422/918 |
| 5,948,610 A | 9/1999 | Ho et al. | | |
| 6,177,266 B1 | 1/2001 | Krishnamurthy et al. | | |
| 6,558,902 B1 | 5/2003 | Hillenkamp | | |
| 6,833,249 B2 | 12/2004 | Khanuja et al. | | |
| 7,020,559 B1 | 3/2006 | Demirev et al. | | |
| 8,735,091 B2 * | 5/2014 | Hyman | ................. | G01N 1/4077 |
| | | | | 435/253.1 |
| 2002/0192676 A1 | 12/2002 | Madonna et al. | | |
| 2008/0009029 A1 | 1/2008 | Govorun et al. | | |
| 2008/0050829 A1 | 2/2008 | Ivey et al. | | |
| 2010/0120085 A1 | 5/2010 | Hyman et al. | | |
| 2011/0268744 A1 | 11/2011 | Garthwaite et al. | | |
| 2012/0165246 A1 | 6/2012 | Lindner et al. | | |
| 2013/0309714 A1 | 11/2013 | Hyman et al. | | |
| 2013/0309716 A1 | 11/2013 | Monnin et al. | | |

FOREIGN PATENT DOCUMENTS

| | | |
|---|---|---|
| WO | WO 2004/014322 | 2/2004 |
| WO | WO 2009/065580 | 5/2009 |
| WO | WO 2011/058131 | 5/2011 |

OTHER PUBLICATIONS

Smithwick et al. Preparation of Acid-Fast Microscopy Smears for Proficiency Testing and Quality Control. Journal of Clinical Microbiology (1978), v8(1), p. 110-111. (Year: 1978).*
Saleeb et al. Identification of Mycobacteria in Solid Culture Media by MALDI TOF MS. J of Clinical Microbiology, May 2011, 1790-1794, vol. 45, No. 9.
Fenselau et al., Characterization of intact microorganisms by MALDI Mass Spectrometry, Mass Spectrometry Reviews, 2001, 157-171, vol. 20, No. 4.
Fox et al, Mass Spectrometry for Species or Strain Identification after Culture or without Culture: Past, Present and Future, J. Clin. Micro, 2006, 2677-2680, vol. 44, No. 8.
Ingebretsen et al., Rapid identification of clinical mycobacterial strains by matrix-assisted laser desorption ionisation-time-of-flight mass spectrometry (MALDI-TOF MS), 22nd European Congress of Clinical Microbiology and Infection Diseases (ECCMID), dated Mar. 29, 2012.
International Search Report for PCT/US2013/041159 dated Jul. 9, 2013.
Khechine et al., Matrix-Assisted Laser Desorption/Ionization Time-of-Flight Mass Spectrometry Mycobacteria Identification of in Routine Clinical Practice, PLOS One, 2011, e24720, vol. 6, No. 9.
Lanigan et al., Mycobacterial proteome extraction: Comparison of disruption methods, Proteomics, 2004, 1094-1100, vol. 4, No. 4.
Lefmann et al., Novel Mass Spectrometry-Based Tool for Genotypic Identification of Mycobacteria, J. Clin. Micro., 2004, 339-346, vol. 42, No. 1.
Ryzhov et al., Rapid Characterization of Spores of *Bacillus cereus* Group Bacteria by Matrix-Assisted Laser Desorption-Ionization Time-of-Flight Mass Spectrometry, 2000, 3828-3834, vol. 66, No. 9.

(Continued)

*Primary Examiner* — Sean C. Barron

(57) ABSTRACT

The present invention is directed to a method and kit for inactivation of acid-fast bacteria. In some embodiments, the method may include: transferring a sample from a liquid culture containing acid-fast bacteria to a first tube, wherein the first tube comprises a body, a first end to the body having an opening, and a second end to the body having a frusto-conical portion ending in a concave tip; centrifuging the tube to pellet the acid-fast bacteria in the concave tip and subsequently decanting a supernatant; resuspending the acid-fast bacteria pellet in alcohol; transferring the suspension to a second tube containing beads; agitating the second tube to disrupt acid-fast bacteria cells; and incubating the suspension to inactivate the acid-fast bacteria in the test sample. The method may also include identifying the acid-fast bacteria with mass spectrometry.

13 Claims, 6 Drawing Sheets

(56) References Cited

OTHER PUBLICATIONS

Buchan et al., Comparison of MALDI-TOF MS with HPLC and Nucleic Acid Sequencing for the Identification of Mycobacterium Species in Cultures Using Solid Medium and Broth, Am. Soc. for Clin. Pathol., 2014, 25-34, 141
Dunne et al., Rapid Inactivation of Mycobacterium and Nocardia Species before Identification Using Matrix-Assisted Laser Desorption Ionization-Time of Flight Mass Spectrometry, J. of Clin. Microbiology, 2014, 3654-3659, vol. 52, No. 10.
Dridi et al., Characterization of prokaryotes using MALDI-TOF mass spectrometry, Methods in Microbiology, 2011, vol. 38, pp. 283-297.
Lotz et al., Rapid identification of mycobacterial whole cells in solid and liquid culture media by matrix-assisted laser desorption ionization-time of flight mass spectrometry, J. of Clin. Microbiology, 2010, vol. 48, No. 12, pp. 4481-4486.
Ayyadurai et al., Rapid identification and typing of *Yersinia pestis* and other *Yersinia* species by matrix-assisted laser desorption/ionization time-of-flight (MALDI-TOF) mass spectrometry, BMC Microbiology, 2010, vol. 10, 7 pages.

\* cited by examiner

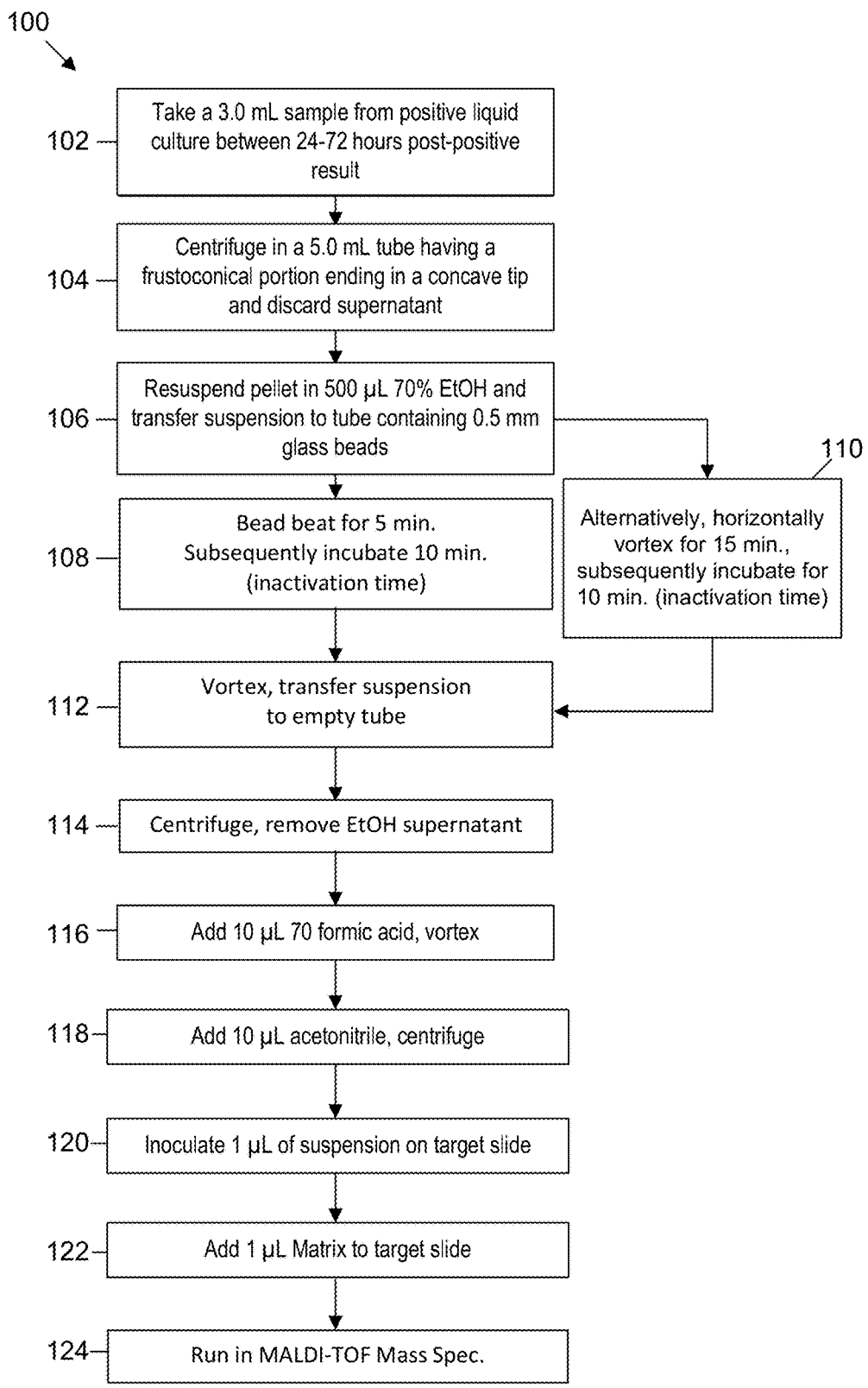
Figure 1. Liquid Media Inactivation/Extraction

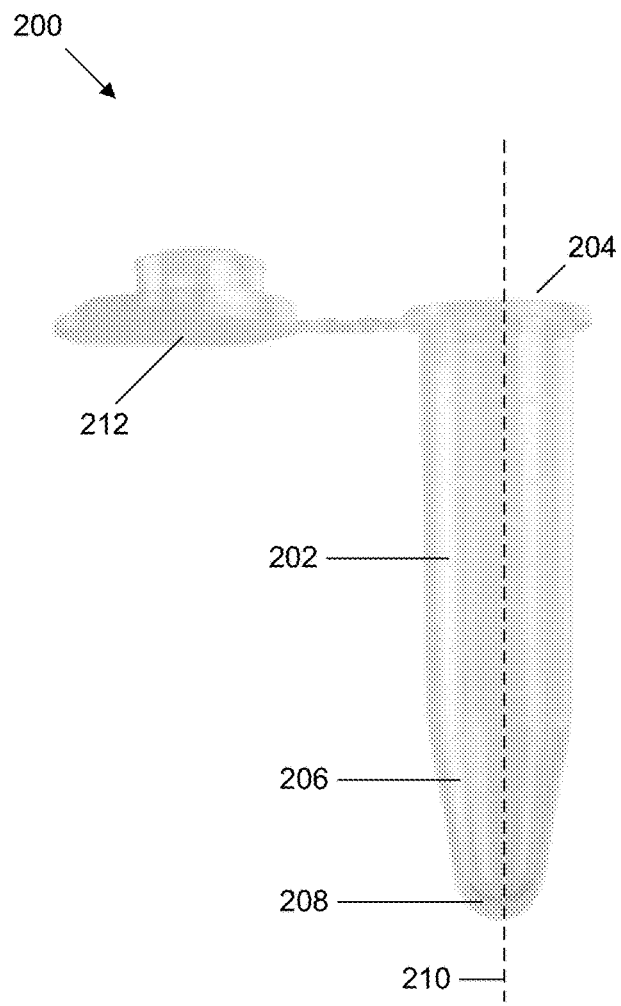
Figure 2. Tube having a frustoconical portion ending in a concave tip

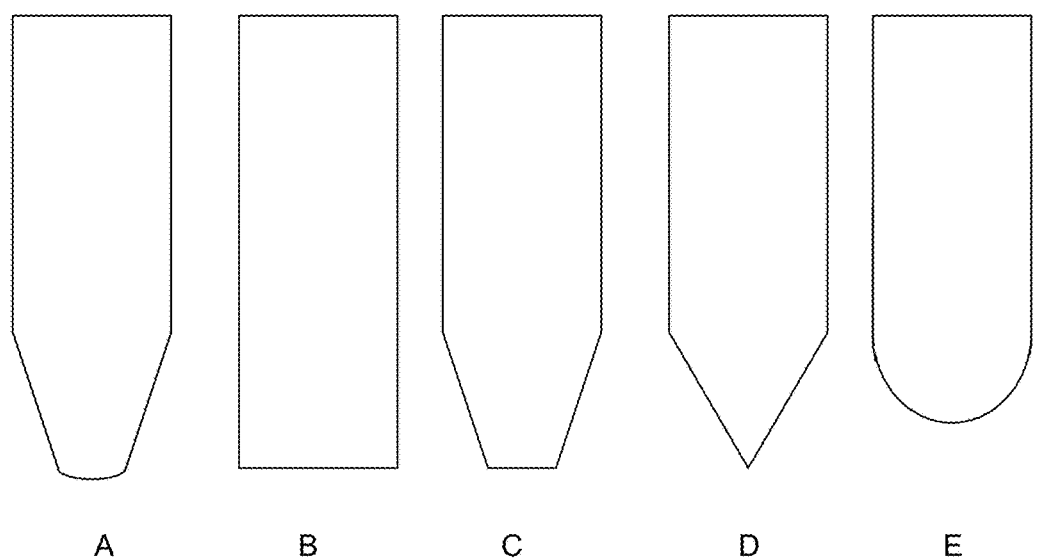
Figure 3. Comparison of tube profiles

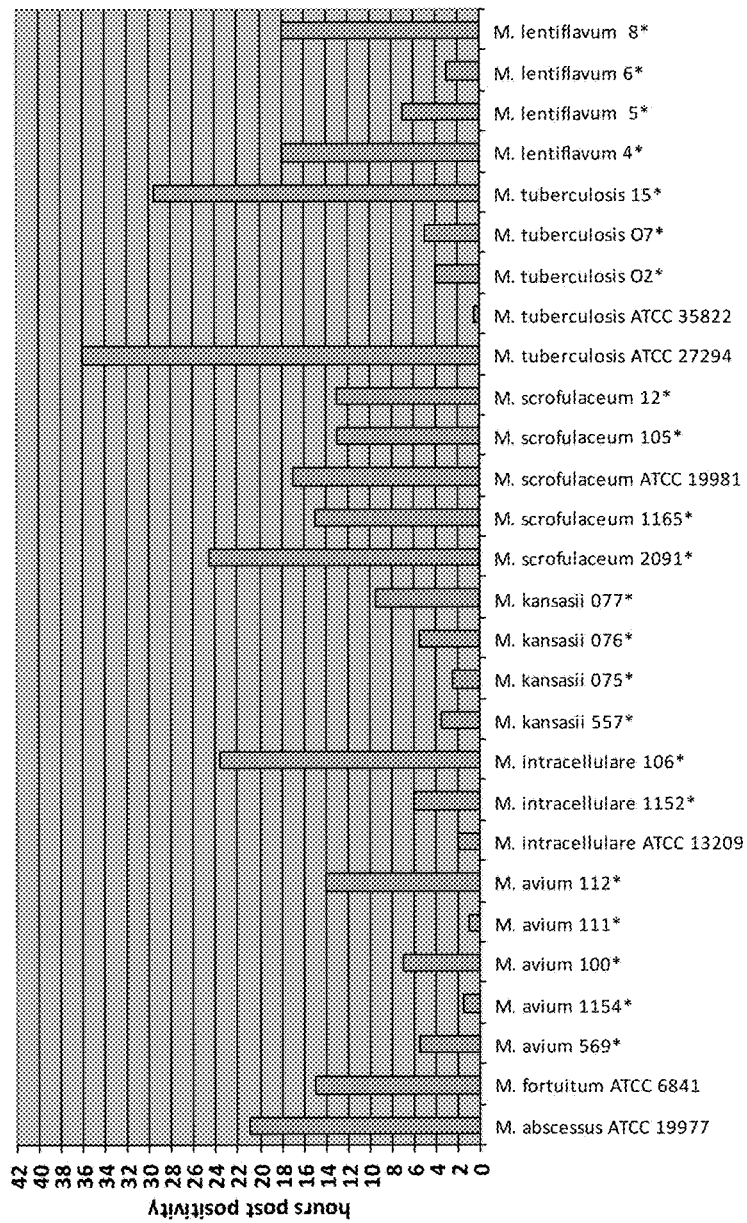
Figure 4. Identification results VersaTREK Mycobacterium
Description: Identification results show the incubation time post positivity where species matched with 99.9% agreement to the expected species level identification.
*Clinical isolates

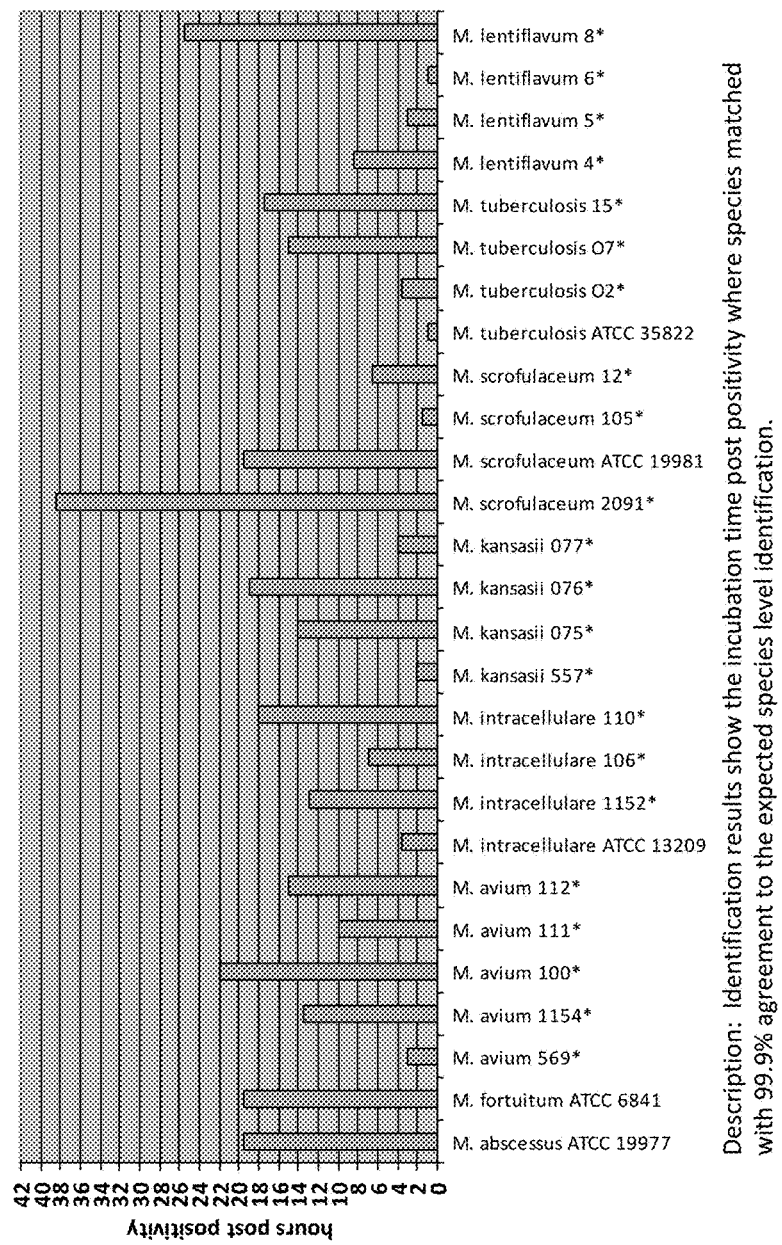
Figure 5. Identification results BBL MGIT 960 Mycobacterium

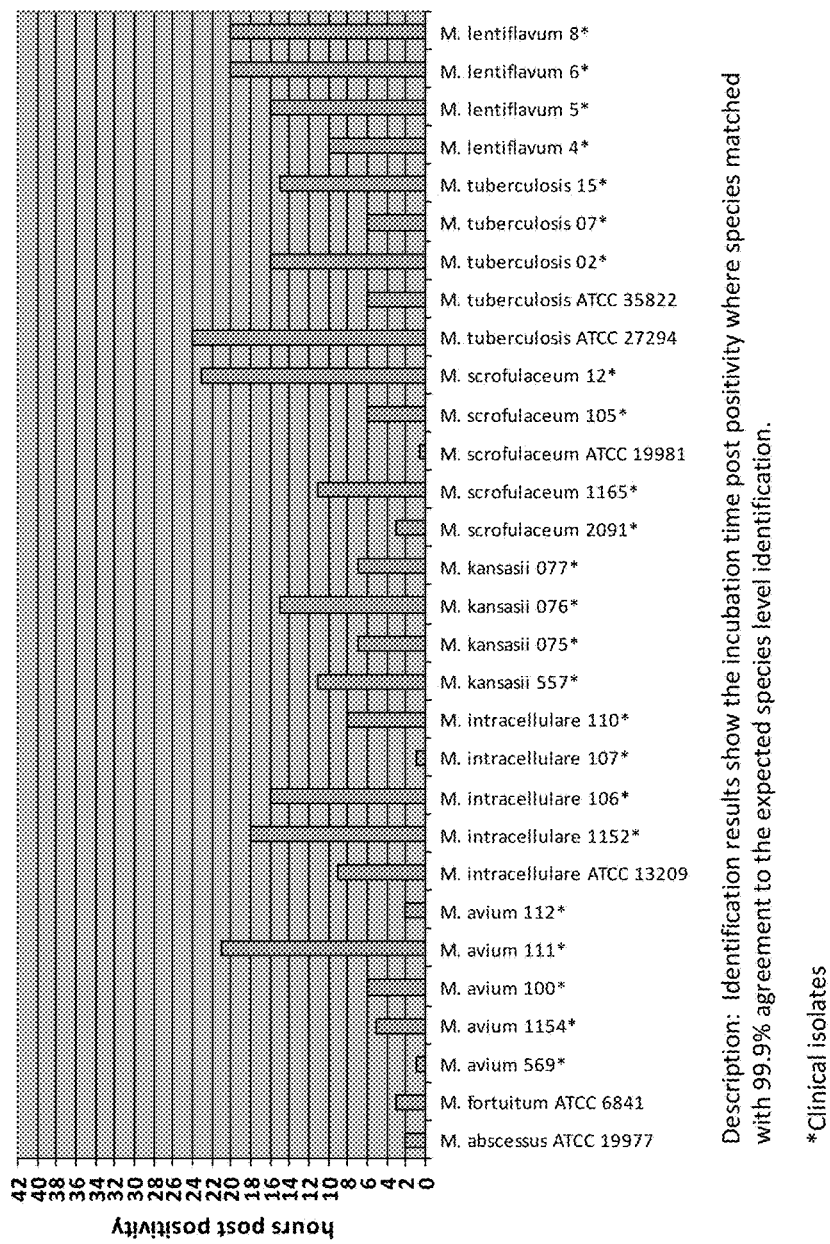
Figure 6. Identification results BacT/ALERT MP Mycobacterium

METHODS FOR INACTIVATION AND EXTRACTION OF ACID-FAST BACTERIA FROM LIQUID MEDIA FOR CHARACTERIZATION AND/OR IDENTIFICATION USING MASS SPECTROMETRY

CROSS REFERENCE TO RELATED APPLICATION

This application claims the benefit of U.S. Provisional Patent Application No. 62/209,116, entitled, "Methods for Inactivation and Extraction of Acid-Fast Bacteria from Liquid Media for Characterization and/or Identification using Mass Spectrometry", filed Aug. 24, 2015, and U.S. Provisional Patent Application No. 62/306,390, entitled "Methods for Inactivation and Extraction of Acid-Fast Bacteria from Liquid Media for Characterization and/or Identification using Mass Spectrometry", filed Mar. 10, 2016, both of which are incorporated herein.

FIELD OF THE INVENTION

The present invention relates to methods for the inactivation and extraction of acid-fast bacteria, such as *Mycobacterium* or *Nocardia*. In particular, the present invention is directed to a method for the rapid characterization and/or identification of *Mycobacterium* or *Nocardia* species grown in liquid media using mass spectrometry.

BACKGROUND OF THE INVENTION

Traditional automated phenotypic ID tests, such as the Vitek®, Phoenix and Microscan® systems, or manual phenotypic tests such as API require that microorganisms be in an appropriate growth phase and free of interfering media and blood products in order to provide robust results. These systems use colonies grown from the positive broth for 18-24 hours on plated media. However, in an effort to obtain faster results, some laboratories have reported using these systems with microorganisms isolated from clinical samples. Faster and more broadly specific tests are urgently needed in order to provide the physician with clinically relevant results.

Identifying microorganisms cultured in liquid media is particularly difficult because of the lower concentration of microorganisms in the sample container and because the liquid media may interfere with analytical methods such as mass spectrometry.

Mass spectrometric methods have the potential to allow for identification of microorganisms very quickly, but may encounter interference from the many compounds present in liquid culture media and in clinical samples such as sputum, sterile body fluids, or combinations thereof.

Other methods for characterization and/or identification of microorganisms have been described, including:

U.S. Pat. No. 6,177,266, which discloses a method for the chemotaxonomic classification of bacteria with genus, species and strain specific biomarkers generated by matrix assisted laser desorption ionization time-of-flight mass spectrometry (MALDI-TOF-MS) analysis of either cellular protein extracts or whole cells.

U.S. Pat. No. 8,735,091, which discloses a method for the inactivation and extraction of acid-fast bacteria, such as *Mycobacterium* and *Nocardia*, from solid and liquid media. The '091 patent, however, does not recognize the difficulty associated with the protein extraction of acid-fast bacteria when grown in liquid media. In particular, the '091 patent does not recognize the difficulty in securing a sufficient amount of biomass of microorganisms from liquid media for identification using mass spectrometry. Further, the '091 patent does not recognize the difficulty in removing the inactivating solution, which interferes with identification using mass spectrometry. The '091 patent does not recognize the unexpected benefits of collection and retention of sufficient biomass of the acid fast bacteria for the inactivation and extraction in a tube having a specific size and/or shape. Finally, the '091 patent does not address the difficulty of separating the pellet from liquid media to avoid interference for identification using mass spectrometry.

Thus, there remains a need in the art for efficient and rapid protocols for the inactivation and/or extraction of microorganisms from liquid media for subsequent analysis, characterization and/or identification by mass spectrometry. In particular, inactivation, or cell death, is often necessary for subsequent handling of acid-fast bacteria, such as *Mycobacterium* and *Nocardia*, outside a Biosafety Level-3 (BSL-3/P3) environment.

SUMMARY OF THE INVENTION

In one aspect, the present invention is directed to a method for inactivation and extraction of acid-fast bacteria (e.g., *Mycobacterium* or *Nocardia* species) in a test sample from liquid media, the method comprising the following sequential steps: (a) transferring a test sample from a liquid culture containing acid-fast bacteria to a first tube, wherein the first tube comprises a body, a first end to the body having an opening, and a second end to the body having a frustoconical portion ending in a concave tip; (b) centrifuging the first tube to pellet the acid-fast bacteria in the concave tip and subsequently decanting a first supernatant, wherein the frustoconical portion ending in the concave tip is configured to retain the pellet of acid-fast bacteria in the concave tip while decanting at least 90% of the first supernatant; (c) resuspending the acid-fast bacteria pellet in alcohol; (d) transferring the suspension from the first tube to a second tube containing beads; (e) agitating the second tube to break up clumps and/or disrupt acid-fast bacteria cells in the second tube; and (f) incubating the suspension for at least about 5 minutes to inactivate the acid-fast bacteria in the test sample.

In one embodiment, the acid-fast bacteria (e.g., *Mycobacterium* or *Nocardia*) pellet can be resuspended in step (c) in from about 50% to about 100% ethanol, for example, the pellet may be resuspended in about 70% ethanol. The method may further comprise bead beating and/or vortexing the container in step (e) for about 1 minute to about 30 minutes. In one embodiment, the beads are 0.5 mm glass beads. In one embodiment, the subsequent incubation step (f) comprises an incubation for at least about 3 minutes, or at least about 10 minutes. In another embodiment, the incubation in step (f) is at room temperature.

In another embodiment, the method may further comprise the following additional sequential steps as part of protein extraction: (g) transferring the suspension to a third tube and centrifuging the third tube to pellet the inactivated acid-fast bacteria and subsequently removing a second supernatant; and (h) resuspending the inactivated acid-fast bacteria pellet to generate a solution comprising the inactivated acid-fast bacteria. In some embodiments, the supernatant from step (h) can be applied directly, or as a water suspension, to a mass spectrometry slide or plate.

The pellet in step (g) may be resuspended using from about 50% to about 90% formic acid, for example, the pellet may be resuspending using 70% formic acid, in step (h). After resuspending the pellet, acetonitrile may be added to obtain a final concentration of acetonitrile of from about 35% to about 65%, for example, to obtain a final concentration of about 50%. In one embodiment, the pellet may be resuspended in 10 µL of formic acid in step (h) and 10 µL of acetonitrile can be added to the resuspended pellet in step (h). In some embodiments, the suspension may be centrifuged to pellet cellular debris as shown in step (i).

In accordance with this embodiment, the method may further comprises the following additional sequential steps: (j) transferring an aliquot of the supernatant from step (i) to a mass spectrometry target slide and adding a matrix solution; and (k) identifying protein profiles of the inactivated acid-fast bacteria on the mass spectrometry slide by mass spectrometry to acquire one or more mass spectra of the acid-fast bacteria and characterizing and/or identifying said acid-fast bacteria in the test sample by comparison of the measured mass spectrum with one or more reference mass spectra. Optionally, step (j) comprises transferring an aliquot (e.g., 1 µL) of the test sample obtained from step (i) to a mass spectrometry slide or plate, allowing the aliquot to dry and subsequently adding a matrix. Any known matrix may be used, for example, the matrix may be alpha-cyano-4-hydroxycinnamic acid (CHCA). In accordance with the present invention, the acid-fast bacteria can be identified to the family, genus, species, strain level and/or group/complex using mass spectrometry, for example, MALDI-TOF mass spectrometry.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE FIGURES

The method and kit of this disclosure will be described in conjunction with the appended drawings, in which:

FIG. 1 shows a flow chart of a method for inactivation and extraction of acid-fast bacteria (e.g., *Mycobacterium* or *Nocardia*) from a liquid media, in accordance with an embodiment of the present invention.

FIG. 2 shows an example of a tube having a frustoconical portion ending in a concave tip, in accordance with an embodiment of the present invention.

FIG. 3 shows examples of tubes having different profiles, in accordance with an embodiment of the present invention.

FIG. 4 shows identification results of various *Mycobacterium* strains incubated in a VersaTREK® Automated Microbial Detection System.

FIG. 5 shows identification results of various *Mycobacterium* strains incubated in a Bactec™ MGIT™ 960 Mycobacterial Detection System.

FIG. 6 shows identification results of various *Mycobacterium* strains incubated in a BacT/ALERT® 3D instrument.

DETAILED DESCRIPTION OF THE INVENTION

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

The present assignee's VITEK® MS system (bioMérieux, Inc., St. Louis, Mo.) provides a platform for bacterial identification using a Matrix Assisted Laser Desorption Ionization—Time of Flight (MALDI-TOF) Mass Spectrometer to analyze the protein profile of a sample and match it to a database of known organism profiles. Samples are deposited onto a target slide, covered with a matrix (e.g., CHCA matrix (α-cyano-4-hydroxy-cinamic acid matrix)), and then processed through the Mass Spectrometer.

Most common clinically-relevant microorganism can be analyzed by depositing cells directly onto the VITEK® MS target slide. The preparation of acid-fast bacteria (e.g., *Mycobacterium* or *Nocardia*) samples for analysis differs from the standard procedure in that an inactivation step is necessary in order to make the samples safe for handling outside of a Biosafety Level-3 (BSL-3/P3) environment. Further, analyzing samples from liquid media results in challenges in securing adequate amounts of biomass as well as clearing inactivating solution that will interfere with identification.

The present applicants have found that incubation in alcohol in conjunction with mechanical disruption provides an effective and rapid method for the inactivation of acid-fast bacteria. Alcohol exposure was shown to be effective when using a process involving an agitation or mechanical disruption step followed by subsequent inactivation step by incubating the disrupted sample in alcohol at room temperature for at least 3 minutes, at least 5 minutes, or at least 10 minutes. In some embodiments, the alcohol is ethanol. In one embodiment, mechanical disruption is performed using a vortex or a Bead Beater (BioSpec, Bartlesville, Ok.), a homogenizer that disrupts cells by agitating a sealed micro centrifuge tube containing sample, extraction solution, and beads (e.g., tiny glass beads). Typically, the beads can be any known beads that can operate to disrupt cells in a container or microcentrifuge tube. For example, the beads can be glass, ceramic, zirconia, silicon, metal, steel, tungsten carbide, garnet, sand, or sapphire beads. In one embodiment, the bead can be from about 0.1 mm to about 1 mm in size, for example, about 0.5 mm in size.

Additional processing steps can then be used to assist in extracting the cellular proteins from the inactivated cells in order to yield clear and consistent spectra. For example, a treatment step in formic acid followed by exposure to acetonitrile can be used to extract and dissolve proteins for subsequent analysis (e.g., by mass spectrometry).

The present invention provides methods for the inactivation, extraction, characterization, and/or identification of an unknown acid-fast bacterium in a test sample from liquid media. The present invention is also directed to a method for the rapid characterization and/or identification of acid-fast bacteria (e.g., *Mycobacterium* or *Nocardia*) in a test sample from liquid media using mass spectrometry. The rapid methods allow for characterization and/or identification of acid-fast bacteria more quickly than prior techniques, resulting in faster diagnoses and characterization/identification of test samples. The steps involved in the methods of the invention, from obtaining a sample to characterization/identification of acid-fast bacteria, can be carried out in a very short time frame to obtain clinically relevant actionable information.

In certain embodiments, the methods of the invention can be carried out in less than about 120 minutes, e.g., in less than about 110, 100, 90, 80, 70, 60, 50, 40, 30, 20, 15, or 10 minutes. The rapidity of the methods of the invention represents an improvement over prior methods.

In one embodiment of the invention, samples are obtained from a subject (e.g., a patient) having or suspected of having an acid-fast bacterial infection. As used herein, the term "acid-fast bacteria" is intended to encompass any acid-fast bacteria including, but not limited to, *Mycobacterium* and *Actinomyces* (including *Nocardia, Rhodococcus, Gordonia, Tsukamurella* and *Dietzia*).

As used herein, the term "mycobacteria" or "*Mycobacterium*" is intended to encompass any known mycobacteria, including, but not limited to, rapid and slow-growing bacteria such as *Mycobacterium tuberculosis, Mycobacterium bovis, Mycobacterium microti, Mycobacterium africanum, Mycobacterium canetti, Mycobacterium avium, Mycobacterium intracellulare, Mycobacterium scrofulaceum, Mycobacterium kansasii, Mycobacterium malmoense, Mycobacterium xenopi, Mycobacterium marinum, Mycobacterium simiae, Mycobacterium terrae, Mycobacterium ulcerans, Mycobacterium abscessus, Mycobacterium fortuitum, Mycobacterium chelonae, Mycobacterium smegmatis, Mycobacterium alvei, Mycobacterium farcinogenes, Mycobacterium fortuitum ssp fortuitum, Mycobacteirum houstonense, Mycobacterium peregrinum, Mycobacterium porcinum, Mycobacterium senegalense, Mycobacterium genavense, Mycobacterium haemophilum, Mycobacterium immunogenum, Mycobacterium lentiflavum, Mycobacterium mucogenicum, Mycobacterium szulgai, Mycobacterium tuberculosis* complex and *Mycobacterium gordonae*. In some embodiments, the rapid growers such as *M. abscessus, M. fortuitum, M. chelonae,* and *M. smegmatis,* can be identified in a short period of time, which assists in diagnosis and treatment. Unexpectedly, slow growing *Mycobacterium* species can also be inactivated and extracted quickly, and then identified in a short period of time, as shown in FIGS. 4-6.

As used herein, the term "*Nocardia*" is intended to encompass any known *Nocardia,* including, but not limited to, *Nocardia aerocolonigenes, Nocardia africana, Nocardia argentinensis, Nocardia asteroids, Nocardia blackwellii, Nocardia brasiliensis, Nocardia brevicatena, Nocardia camea, Nocardia caviae, Nocardia cerradoensis, Nocardia corallina, Nocardia cyriacigeorgica, Nocardia dassonvillei, Nocardia elegans, Nocardia farcinica, Nocardia nigiitansis, Nocardia nova, Nocardia opaca, Nocardia otitidis-cavarium, Nocardia paucivorans, Nocardia pseudobrasiliensis, Nocardia rubra, Nocardia seriolae, Nocardia transvelencesis, Nocardia uniformis, Nocardia vaccinii,* and *Nocardia veterana*.

As used herein, "characterization" encompasses the broad categorization or classification of biological particles and/or the actual identification of a family, genus, species, and/or strain level or groups/complex of an acid-fast bacteria. Classification may comprise determination of phenotypic and/or morphologic characteristics for the acid-fast bacteria. For example, characterization of the bacteria may be accomplished based on observable differences, such as composition, shape, size, pigmentation, clustering, and/or metabolism.

As used herein "identification" means determining to which family, genus, species, strain or group/complex of a previously unknown acid-fast bacteria (e.g., *Mycobacterium* or *Nocardia*) belongs to. For example, identifying a previously unknown acid-fast bacteria to the family, genus, species, strain level, and/or groups/complex.

In an embodiment, the present invention is directed to a method for inactivation of an acid-fast bacteria contained in a liquid culture medium. In one embodiment, the method comprises the following steps: (a) transferring a test sample from a liquid culture containing acid-fast bacteria to a first tube, wherein the first tube comprises a body, a first end to the body having an opening, and a second end to the body having a frustoconical portion ending in a concave tip; (b) centrifuging the first tube to pellet the acid-fast bacteria in the concave tip and subsequently decanting a first supernatant, wherein the frustoconical portion ending in the concave tip is configured to retain the pellet of acid-fast bacteria in the concave tip while decanting at least 90% of the first supernatant; (c) resuspending the acid-fast bacteria pellet in alcohol; (d) transferring the suspension to a second tube containing beads, (e) agitating the second tube to break up clumps and/or disrupt acid-fast bacteria cells in the second tube; and (f) incubating the suspension for at least about 5 minutes to inactivate the acid-fast bacteria in the test sample.

In one embodiment, the liquid culture sample acquired may be from about 0.5 mL to about 10 mL, from about 1 mL to about 5 mL, from about 1 mL to about 3 mL, or about 1, 2, 3, 4, or 5 mL. In an exemplary embodiment, the sample taken from the positive liquid culture medium is about 3 mL. It has been found that a sample comprising at least about 3 mL from the liquid culture sample has sufficient microorganisms present to yield an accurate identification via mass spectrometry.

In some embodiments, the liquid culture containing acid-fast bacteria is a sample container that has tested positive for acid-fast bacteria. For example, the sample container may culture a biological sample from a subject. If the subject is positive for acid-fast bacteria, the sample container is identified as positive via, e.g., a sensor in the container. In one embodiment, the liquid culture sample is acquired at least about 24 hours after the sample container is identified as positive. In some embodiments, the liquid culture sample is acquired between about 24 hours and 72 hours after the sample container is identified as positive. In further embodiments, the liquid culture sample is acquired 1 hour, 2 hours, 4 hours, 6 hours, 9 hours, 12 hours, 15 hours, 18 hours, 21 hours, or 24 hours after the sample container is identified as positive. In still further embodiments, the liquid culture sample is acquired later than 48 hours after the sample container is identified as positive. In some embodiments, allowing a sample container to continue to incubate after it has been identified as positive causes an increase in the population size of the microorganisms in the sample container. For example, in some embodiments a minimum concentration of $1.0 \times 10^7$ CFU/mL is present in the sample as required biomass for acid-fast bacteria. In this way, the concentration of microorganisms in the liquid culture sample will be greater and the likelihood of an accurate identification via mass spectrometry increases. Further, some laboratories may have times during the day or week when sample containers cannot be evaluated. The instant method is flexible in the length of time that a sample container may be incubated after it has been identified as positive.

As discussed, in some embodiments the method includes centrifuging the sample in a tube having a body, a first end to the body having an opening, and a second end to the body having a frustoconical portion ending in a concave tip. Turning briefly to FIG. 2, an exemplary tube as described is shown. In FIG. 2, the tube 200 includes the body 202, the opening 204 at the first end of the body 202, and frustoconical portion 206 ending in a concave tip 208 at the second end of the body 202 along a longitudinal axis 210 of the tube 200. In an embodiment, the body has a volume of about 5 mL. For example, the body may have a volume of 3 mL, 4 mL, 5 mL, 6 mL, or 7 mL. As used herein, "frustoconical" means the shape of the frustum of a cone. The frustum of a cone is the basal part of a cone formed by cutting off the top by a plane parallel to the base. In some embodiments, the tube 200 includes a resealable cap 212 for securing the contents of the tube 200 which may be further secured via a safety lock. In some embodiments, the resealable cap may be a screw cap. In this embodiment, the screw cap seals the microorganism in the first tube to protect the user. For example, the screw cap may form a hermetic seal to reduce the chance of infection. In further embodiments, the resealable cap may be a snap fit cap and may include features so as an O-ring seal or a twist-lock.

In some embodiments, the angle of the frustoconical portion 206 from the longitudinal axis 210 is less than 45 degrees. For example the angle of the frustoconical portion 206 from the longitudinal axis can be about 30 degrees, about 25 degrees, about 20 degrees, about 15 degrees, about 10 degrees, or about 5 degrees. The angle of the frustoconical portion 206 relative to the longitudinal axis 210 assists in decanting supernatant from the tube while retaining a pelleted microorganism in the concave tip. In some embodiments, the concave tip is configured to retain the pelleted microorganism while decanting supernatant (e.g., liquid media, etc.).

In some embodiments, the first tube is centrifuged for at least about 10 minutes, For example, the first tube may be centrifuged for 5 minutes, 10 minutes, 15 minutes, etc. In an embodiment, the first tube is centrifuged at 3,000×g to generate a pellet at the bottom of the tube and a supernatant above the pellet. The first tube may be centrifuged at a faster or slower rate, as determined by one of skill in the art.

In some embodiments, after centrifuging the sample in the first tube, a first supernatant resulting from the centrifugation is decanted from the first tube, wherein the frustoconical portion ending in the concave tip is configured to retain the pellet of acid-fast bacteria in the concave tip. In some embodiments, at least about 90% of the first supernatant is decanted. For example, 90%, 95%, 99%, or 99.9% of the supernatant is decanted from the first tube. Removal of the supernatant and retention of the pelleted microorganism is important for accurate identification of the microorganism using mass spectrometry. Removal of the supernatant is important because excessive supernatant in the biological sample can interfere with the spectra produced using the mass spectrometer. Retention of the pelleted microorganism is important to ensure that sufficient microorganism is available for the mass spectrometer analysis. In some embodiments, decanting includes blotting the first tube and/or inverting the first tube for a period of time so that the supernatant can exit the opening.

After the centrifugation step (b), the acid-fast bacteria pellet can be resuspended in step (c) in the first tube with from about 10 µL to about 1 mL of alcohol, or with about 50 µL to about 750 µL, with about 100 µL to about 500 µL, or with about 500 µL. The alcohol used for resuspending the pellet can be from about 50% to about 100% alcohol, from about 60% to about 90% alcohol, or about 50%, 60%, 70%, 80% or 90% alcohol. In an exemplary embodiment, the alcohol is ethanol.

In some embodiments, the method includes transferring the suspension from the first tube to a second tube containing beads. In some embodiments, the method includes agitating the suspension to break up clumps and/or disrupt acid-fast bacteria cells. For example, the acid-fast bacteria test sample can be subjected to mechanical disruption using a vortex or a bead beater (e.g., Bead Beater, BioSpec, Bartlesville, Ok.), a homogenizer that disrupts cells by agitating a sealed micro centrifuge tube containing sample, extraction solution, and beads. Typically, the beads can be any known beads that can operate to disrupt cells in a container or microcentrifuge tube. For example, the beads can be glass, ceramic, zirconia, silicon, metal, steel, tungsten carbide, garnet, sand, or sapphire beads. In one embodiment, the bead can be from about 0.1 mm to about 1 mm in size, for example, about 0.5 mm in size. In one embodiment, the beads are 0.5 mm glass beads. Typically, the tube is subjected to disruption by beating or vortexing the container in step (e) for about 1 minute to about 30 minutes, for about 5 minutes to about 20 minutes, for about 5 minutes to about 10 minutes, or for about 5 minutes or 10 minutes. In further embodiments, the tube is agitated using a vortex for a period of time. For example, the tube may be vortexed for at least about 15 minutes. In some embodiments, the tube is vortexed for 10 minutes, 15 minutes, 20 minutes, 30 minutes, or longer.

After the acid-fast bacteria in the test sample have been disrupted, the tube, and thus the acid-fast bacteria (e.g., *Mycobacterium* or *Nocardia*) in the test sample, are subjected to inactivation by incubating the container for at least 3 minutes. In one embodiment, the incubation step (f) can be for at least 5 minutes or for at least 10 minutes. In another embodiment, the incubation step (f) can be for about 5 minutes to about 30 minutes, for about 10 minutes to about 20 minutes, or for about 5, 10, 15, 20, 25, or 30 minutes. In one embodiment, the incubation step (f) is at room temperature. In another embodiment, the incubation step (f) is at an elevated temperature, e.g., 30 degrees Celsius, 37 degrees Celsius, or 55 degrees Celsius.

In another aspect, the present invention is directed to further steps for protein extraction of an acid-fast bacteria test sample. In one embodiment, the acid-fast bacteria test sample subjected to the extraction steps of the present invention can be the test sample obtained from the previously described method for inactivation (i.e., the inactivated acid-fast bacteria test samples described above).

The extraction method may comprise the following steps: (g) transferring the suspension to a third tube and centrifuging the third tube to pellet the inactivated acid-fast bacteria (e.g., *Mycobacterium* or *Nocardia*) and subsequently removing a second supernatant; and (h) resuspending the inactivated acid-fast bacteria pellet to generate a solution comprising the inactivated acid-fast bacteria. In some embodiments, the inactivated acid-fast bacteria pellet is resuspended in formic acid and/or acetonitrile. Optionally, the method further comprises centrifugation of the test sample in the container after step (h) to extract cellular protein (step (i)) and pellet cellular debris. For example, the third tube can be centrifuged for 2 minutes at 16,000×g.

In accordance with these embodiment, the pellet may be resuspended using from about 50% to about 100% formic acid, from about 60% to about 90% formic acid, or about 50%, 60%, 70%, 80%, 90% or 100% formic acid. In some embodiments, after resuspending the pellet acetonitrile is added to obtain a final concentration of from about 35% to about 65%, to obtain a final concentration of from about 40% to about 60%, or to obtain a final concentration of about 35%, 40%, 50%, 60%, or 65% acetonitrile. In one embodiment, 100% acetonitrile is used for this step although other concentrations of acetonitrile may be used.

In one embodiment, the pellet may be resuspended in at least about 3, 5, or 10 μL of formic acid and at least 3, 5 or 10 μL of acetonitrile can be added to the resuspended pellet. In another embodiment, the pellet may be resuspended using from about 3 μL to about 100 μL of formic acid, about 5 μL to about 80 μL formic acid, about 10 μL to about 50 μL of formic acid, or about 3, 5, 10, 15, 20, 25, 30, 40, 50, 60, 70, 80, 90 or 100 μL formic acid. In another embodiment, after resuspending the pellet, at least about 3, 5 or 10 μL of acetonitrile are added to the resuspended pellet. For example, from about 3 μL to about 100 μL acetonitrile, from about 5 μL to about 80 μL acetonitrile, 10 μL to about 50 μL acetonitrile, or about 3, 5, 10, 15, 20, 25, 30, 40, 50, 60, 70, 80, 90 or 100 μL acetonitrile, may be added to the resuspended sample.

The present invention also provides methods for characterization and/or identification of an unknown acid-fast bacteria (e.g., *Mycobacterium* or *Nocardia*) using mass spectrometry, e.g., using matrix assisted laser desorption ionization time-of-flight (MALDI-TOF mass spectrometry). In accordance with the present invention, the characterization and/or identification steps may follow the inactivation and extraction steps described above.

In accordance with this embodiment, the methods may further comprise the following additional steps: transferring an aliquot of the supernatant from step (j) to a mass spectrometry target slide and adding a matrix solution to the supernatant; and (k) identifying the protein profiles of the inactivated acid-fast bacteria in the third supernatant on the mass spectrometry slide by mass spectrometry to acquire one or more mass spectra of the acid-fast bacteria, and characterizing and/or identifying said acid-fast bacteria in the test sample by comparison of the measured one or more mass spectra with one or more reference mass spectra. Optionally, the transferred aliquot can be from about 0.5 μL to about 2.5 μL, or about 1 μL. As is well known in the art, the aliquot is typically allowed to dry and subsequently a matrix solution is added. In general, any known matrix in the art can be used. For example, in one embodiment, the matrix is alpha-cyano-4-hydroxycinnamic acid (CHCA). In accordance with the present invention, the acid-fast bacteria (e.g., *Mycobacterium* or *Nocardia*) can be identified to the family, genus, species, strain level or group/complex using, for example, MALDI-TOF mass spectrometry, as described further hereinbelow.

After the mass spectrometry plate or slide has been prepared, the slide or plate is inserted into the mass spectrometer. After the time required to pump the sample down (i.e. remove atmospheric gases from the sample so that it is in an environment of 10-5 to 10-7 torr), the sample is introduced into the ionization chamber of the mass spectrometer. The sample is aligned with the system. When optimal alignment is achieved, the nitrogen laser is pulsed. The absorption of the laser energy by the matrix causes it to ablate from the plate's surface due to the high energy deposited. As a side effect, portions of the acid-fast bacteria cells (e.g. proteins) are also vaporized and ionized in the process. These ions are accelerated to a known kinetic energy by the generation of an electrostatic field between the plate and the entrance to the mass spectrometer's flight tube. All singly charged ions, regardless of mass, will have the same kinetic energy at the entrance to the flight tube, but they will have velocities that are inversely proportional to their masses. From there, ions move down the flight tube towards the detector, and lighter ions will arrive before heavier ions (the flight tube is the mass/charge discriminator). The detector generates an electrical charge every time an ion impacts the detector. The output of the detector is digitized and the output displays mass/charge ratio on one axis and number of impacts on the other axis. In one embodiments, the protein profile of the acid-fast bacteria on the slide or plate can be interrogated using any known mass spectrometry techniques, such as MALDI-TOF mass spectrometry, desorption electrospray ionization (DESI) mass spectrometry, GC mass spectrometry, LC mass spectrometry, electrospray ionization (ESI) mass spectrometry and Selected Ion Flow Tube (SIFT) spectrometry, or other mass spectrometry technique.

In some embodiments, control measurements are taken for known acid-fast bacteria, thus allowing for correlation of measured test data with characterization of the acid-fast bacteria of interest using various mathematical methods. For example, the data from samples may be compared with the baseline or control measurements utilizing software systems. More particularly, the data may be analyzed by a number of multivariate analysis methods, such as, for example, General Discriminant Analysis (GDA), Partial Least Squares Discriminant Analysis (PLSDA), Partial Least Squares regression, Principal Component Analysis (PCA), Parallel Factor Analysis (PARAFAC), Neural Network Analysis (NNA), and/or Support Vector Machine (SVM). These methods may be used to classify unknown acid-fast bacteria (e.g., *Mycobacterium* or *Nocardia*) of interest into relevant groups based on existing nomenclature, and/or into naturally occurring groups based on the organism's metabolism, pathogenicity and/or virulence. In one embodiment, after acquisition of a one or more mass spectra for acid-fast bacteria, the one or more mass spectra can be input into the "SARAMIS" microorganism identification software (bioMérieux, Inc., St. Louis, Mo.) for analysis, and thus, for characterization and/or identification of the acid-fast bacteria.

In yet another embodiment, non-spectroscopic measurements from the detection system, such as detection times and growth rates can be used to assist in the characterization and/or identification of acid-fast bacteria from the test sample.

In some embodiments of the invention, characterization and/or identification of the acid-fast bacteria in the test sample need not involve identification of an exact species. Characterization may encompass the broad categorization or classification of biological particles as well as the actual identification of a single species. As used herein "identification" means determining to which family, genus, species, strain level or group/complex a previously unknown acid-fast bacteria belongs to. For example, identifying a previously unknown acid-fast bacteria to the family, genus, species, strain level or group/complex.

Turning now to FIG. 1, in one aspect a method 100 for inactivation, extraction, and identification of acid-fast bacteria in a liquid test sample is provided. In an embodiment, the method includes the following steps: (a) transferring a test sample from a liquid culture medium containing acid-fast bacteria to a first tube, wherein the first tube comprises a body, a first end to the body having an opening, and a second end to the body having a frustoconical portion ending in a concave tip; (b) centrifuging the first tube to pellet the acid-fast bacteria in the concave tip and subsequently decanting a first supernatant; (c) resuspending the acid-fast bacteria pellet in alcohol to generate a suspension; (d) transferring the suspension to a second tube containing beads for mechanical disruption; (e) incubating the suspension in alcohol to inactivate the acid-fast bacteria; (f) transferring the suspension to a third tube; (g) centrifuging the third tube to pellet the inactivated acid-fast bacteria and subsequently removing a second supernatant; (h) resuspending the inactivated acid-fast bacteria pellet in to generate a solution comprising the inactivated acid-fast bacteria; (i) extracting cellular proteins from the solution comprising inactivated acid-fast bacteria and centrifuging the solution to pellet the cellular debris; (g) transferring an aliquot of a third supernatant from step (i) to a mass spectrometry target slide; and (h) interrogating the mass spectrometry target slide by mass spectrometry to acquire one or more mass spectra of protein profiles of the acid-fast bacteria and characterizing and/or identifying said acid-fast bacteria in the test sample by comparison of the measured one or more mass spectra with one or more reference mass spectra of protein profiles.

Turning to block 102, in some embodiments the method includes taking a 3.0 mL sample from a positive liquid culture between 24-72 hours post positive result. As discussed, the volume of the sample assists in ensuring sufficient microorganisms are present in the sample to acquire an acceptable spectra using a mass spectrometry instrument. Similarly, taking the sample from the positive liquid culture between 24 and 72 hours after a positive result increases the population size of the microorganisms in the liquid culture. In some embodiments, the sample may be taken from the positive liquid culture in less than 24 hours. For example, see FIGS. 4-6 showing that many strains of *Mycobacterium* can be identified in as little as two hours post-positive.

In block 104, in some embodiments the sample is placed into a tube (e.g., a 5.0 mL tube) having a frustoconical portion ending in a concave tip, which is then centrifuged. For example, the tube can be centrifuged for 10 minutes at 3,000×g to generate a pellet in the concave tip and a supernatant above the pellet. The supernatant is then discarded by decanting. For example, the tube may be inverted and the supernatant poured off through the opening and then the tube blotted to remove excess liquid.

In block 106, the pellet is resuspended in alcohol. In some embodiments, the pellet is resuspended in 500 µL 70% ethanol and the suspension is transferred to a second tube containing 0.5 mm glass beads, in one embodiment. In some embodiments, the glass beads are added to the original tube. In these embodiments, the alcohol begins to inactivate the microorganism but the cells may still be clumped together in the suspension. As a result, the initial alcohol treatment is not as effective as a treatment after agitation.

In block 108, in one embodiment the tube is bead beat and then incubated. For example, the tube may be bead beat for 5 minutes and then incubated for 10 minutes. The combination of agitation and incubation inactivates the microorganism. Alternatively, as shown in block 110, in some embodiments the tube is vortexed and then incubated, such as vortexed for 15 minutes and then incubated for 10 minutes. As discussed, the incubation may be at room temperature or may be at an elevated temperature.

Turning now to block 112, in some embodiments the inactivated acid-fast bacteria present in the tube after agitation and incubation are vortexed and the suspension is transferred to an empty tube. In block 114, the suspension is centrifuged and the ethanol supernatant is removed, leaving the inactivated acid-fast bacteria pelleted in the tube.

In blocks 116 and 118, cellular proteins are extracted by the addition of 10 µL 70% formic acid and then the addition of 10 µL acetonitrile. In some embodiments, the tube is vortexed after the addition of the formic acid and/or acetonitrile to pellet cellular debris.

In block 120, 1 µL of the suspension is inoculated onto a mass spectrometry target slide, matrix is added to the target slide in block 122, and the microorganism is identified using MALDI-TOF mass spectrometry in block 124. This method describes an unexpected improvement in identification of microorganisms from liquid media using specific steps that address the difficulties of conducting identification from liquid media.

Turning now to FIG. 3, a comparison 300 of tube profiles is provided. As shown in FIG. 3, tube A has a frustoconical portion ending in a concave tip. This profile is in contrast to tubes B, C, D, and E. Tube A has been found to both retain the pellet in the concave tip while decanting a large percentage of the supernatant to assist in identification of microorganisms using mass spectrometry. Tube B, for example, would not be appropriate for identification because some or all of the pellet would be lost during decanting of the supernatant. The tip of tube C is not designed to retain the pellet during decanting while reducing retention of the supernatant. Instead, supernatant will be retained underneath and around the pellet due to the shape of the tip. Similarly, tube D may retain the pellet but would also retain fluid beneath the pellet in the angled tip. For example, after decanting tube A, only 10-20 µL of media remained in the tube in one experiment, but decanting tube D resulted in 200-400 µL of media remaining in the tube after decanting. Tube E results in the loss of some or all of the pellet during the decanting step. Unexpectedly, tube A demonstrates significantly improved results in identifying microorganisms with a mass spectrometry instrument while addressing the difficulties of using liquid media.

In FIG. 4, identification results of multiple strains including ATCC and clinical isolates of *Mycobacterium* species incubated in a VersaTREK® Automated Microbial Detection System are provided. In this Figure, twenty-eight different *Mycobacterium* strains were incubated in the VersaTREK® Automated Microbial Detection System. Each strain was incubated in a sample container using the VersaTREK® Automated Microbial Detection System, removed when the system indicated that the sample container was positive for microorganism growth, incubated for additional periods of time in the sample containers, and samples from the sample containers were intermittently treated via the method disclosed herein to inactivate and extract the proteins from *Mycobacterium* cells. The mycobacterial proteins were then analyzed via MALDI-TOF mass spectrometry to determine if the post-positive sample had sufficient biomass and lack of contamination to yield accurate mass spectra. The results shown in FIG. 4 demonstrate that the method disclosed herein is able to inactivate and extract mycobacterial proteins in a short period of time after the system identifies the sample container as positive for microorganism growth, and accurately produce spectra that match with 99.9% agreement to the expected species level identification. All strains tested were correctly identified when processed within 36 hours post-positivity, and all but three of the strains were identified within 24 hours. Surprisingly, many of the strains, including high prevalence strains such as *M. avium* and *M. intracellulare*, had correct identification when processed within 12 hours post-positivity.

FIG. 5 shows identification results of various *Mycobacterium* strains incubated in a Bactec™ MGIT™ 960 Mycobacterial Detection System. Similar to FIG. 4, FIG. 5 demonstrates that the method is capable of inactivating, extracting, and identifying mycobacterial proteins quickly post-positivity. For example, all but two of the strains had sample spectra that were a 99.9% match to the expected species level identification within 24 hours. The two remaining strains had 99.9% agreement to the expected species level identification within 40 hours. This rapid inactivation, extraction, and identification of mycobacterial proteins will impact the treatment of infections related to mycobacteria.

In FIG. 6, identification results of various *Mycobacterium* strains incubated in a BacT/ALERT® 3D instrument are provided. Again, the samples are incubated in sample containers, the instrument determines when the sample is positive for microorganism growth, and samples are taken from the positive sample containers intermittently for testing via the disclosed method. In this example, all strains had sample spectra that were a 99.9% match to the expected species level identification within 24 hours.

In another aspect, a kit for use with the method described in FIG. 1 and elsewhere herein is provided. In some embodiments, the kit includes a first tube having a body, a first end to the body having an opening, and a second end to the body having a frustoconical portion ending in a concave tip, wherein the first tube has a volume of at least 5 mL; a solution of alcohol; a solution of formic acid; and a solution of acetonitrile. In further embodiments, the kit may include 0.5 mm glass beads and/or blotting paper. Similarly, the kit may include a stand for decanting the first tube or instructions to the method described herein and for which the kit is designed to be used.

In the drawings, the thickness of lines, layers, features, components and/or regions may be exaggerated for clarity. In addition, the sequence of operations (or steps) is not limited to the order presented in the claims unless specifically indicated otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. While the term "comprising" may be used herein, it should be understood that the objects referred to as "comprising" elements may also "consist of" or "consist essentially of" the elements. As used herein, the term "and/or" includes any and all combinations of one or more of the associated listed items. Like numbers refer to like elements throughout. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The present invention is described in part with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The flowcharts and block diagrams of certain of the figures herein illustrate exemplary architecture, functionality, and operation of possible implementations of embodiments of the present invention. It should be noted that in some alternative implementations, the steps noted in the blocks may occur out of the order noted in the figures. For example, two blocks shown in succession may in fact be executed substantially concurrently or the blocks may sometimes be executed in the reverse order or two or more blocks may be combined, depending upon the functionality involved.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. A method for inactivation and extraction of acid-fast bacteria in a test sample, the method comprising the following sequential steps:
   (a) transferring a test sample from a liquid culture containing acid-fast bacteria to a first tube, wherein the first tube comprises a body having a volume of 5 mL, a first end to the body having an opening, and a second end to the body having a frustoconical portion ending in a concave tip;
   (b) centrifuging the first tube to pellet the acid-fast bacteria in the concave tip and subsequently decanting a first supernatant, wherein the frustoconical portion ending in the concave tip is configured to retain the pellet of acid-fast bacteria in the concave tip while decanting at least 90% of the first supernatant;
   (c) resuspending the acid-fast bacteria pellet in alcohol to generate a first suspension;

(d) transferring the suspension from the first tube to a second tube containing beads to form a second suspension;

(e) agitating the second tube to break up clumps and disrupt acid-fast bacteria cells in the second suspension; and (f) incubating the second suspension for at least about 5 minutes to inactivate the acid-fast bacteria in the test sample to form an inactivated second suspension.

2. The method of claim 1, further comprising the following step:

(g) transferring the inactivated second suspension to a third tube and centrifuging the third tube to pellet the inactivated acid-fast bacteria and subsequently removing a second supernatant.

3. The method of claim 2, further comprising the following steps:

(h) resuspending the inactivated acid-fast bacteria pellet to generate a solution comprising the inactivated acid-fast bacteria;

(i) extracting cellular proteins from the solution comprising inactivated acid-fast bacteria and centrifuging the solution to pellet the cellular debris;

(j) transferring an aliquot of a third supernatant from step (i) to a mass spectrometry target slide; and (k) identifying protein profiles of the inactivated acid-fast bacteria on the mass spectrometry slide using a mass spectroscopy instrument.

4. The method of claim 1, wherein at least 99% of the first supernatant is removed in step (b).

5. The method of claim 1, wherein said acid-fast bacteria is *Mycobacterium* or *Nocardia*.

6. The method as claimed in claim 1, wherein said alcohol is ethanol.

7. The method as claimed in claim 1, wherein step (e) comprises agitating the second tube using a bead beater or vortex and beads, wherein said beads are 0.5 mm glass beads.

8. The method as claimed in claim 2, wherein the pellet in step (g) is re-suspended in formic acid.

9. The method as claimed in claim 8, wherein acetonitrile is added to the re-suspended inactivated acid-fast bacteria to a final concentration of from 35% to 65%.

10. The method of claim 1, wherein the method further comprises incubating the suspension in step (f) for at least about 10 minutes at room temperature.

11. The method of claim 3, wherein said acid-fast bacteria sample is identified to the family, genus, species, strain level and/or group/complex.

12. The method of claim 3, further comprising interrogating the test sample on the slide by mass spectrometry to acquire one or more mass spectra of the acid-fast bacteria and characterizing and/or identifying said acid-fast bacteria in the test sample by comparison of the measured one or more mass spectra with one or more reference mass spectra.

13. A method for inactivation and extraction of acid-fast bacteria in a test sample, the method comprising the following sequential steps:

(a) transferring a 3 mL test sample from a positive liquid culture containing acid-fast bacteria to a first tube within 24-72 hours a post-positive result, wherein the first tube comprises a body having a volume of 5 mL, a first end to the body having an opening, and a second end to the body having a frustoconical portion ending in a concave tip;

(b) centrifuging the first tube to pellet the acid-fast bacteria in the concave tip and subsequently decanting a first supernatant, wherein the frustoconical portion ending in the concave tip is configured to retain the pellet of acid-fast bacteria in the concave tip while decanting at least 90% of the first supernatant;

(c) blotting the first tube to remove excess liquid;

(d) resuspending the acid-fast bacteria pellet in alcohol to generate a first suspension;

(e) transferring the suspension from the first tube to a second tube containing beads to form a second suspension;

(f) agitating the second tube to break up clumps and disrupt acid-fast bacteria cells in the second suspension;

(g) incubating the second suspension for at least about 5 minutes to inactivate the acid-fast bacteria in the test sample to form an inactivated second suspension.

* * * * *